United States Patent [19]
Schmidt et al.

[11] Patent Number: 6,167,258
[45] Date of Patent: Dec. 26, 2000

[54] PROGRAMMABLE WIRELESS DATA ACQUISITION SYSTEM

[75] Inventors: Robert N. Schmidt; Donald C. Ferencz, both of Cleveland; Steven P. Hendrix, Sagamore Hills, all of Ohio

[73] Assignee: Cleveland Medical Devices Inc., Cleveland, Ohio

[21] Appl. No.: 09/168,571

[22] Filed: Oct. 9, 1998

[51] Int. Cl.⁷ .......................... H04M 3/00; H04M 11/00; H04Q 7/20; G08L 19/16
[52] U.S. Cl. .......................... 455/419; 455/418; 455/423; 340/870.01; 379/106.01
[58] Field of Search .................... 600/301, 300; 340/870.01, 500, 573, 573.1; 128/903; 455/423, 419, 418, 420, 35.1, 68, 69, 70, 71, 72, 88; 379/106.01, 106.02, 106.03

[56] References Cited

U.S. PATENT DOCUMENTS

| | | | |
|---|---|---|---|
| 5,121,041 | 6/1992 | O'Sullivan | 455/557 |
| 5,295,178 | 3/1994 | Nickel et al. | 455/561 |
| 5,333,177 | 7/1994 | Braitberg et al. | 455/559 |
| 5,375,604 | 12/1994 | Kelly et al. | 600/484 |
| 5,381,804 | 1/1995 | Shambroom | 600/544 |
| 5,417,222 | 5/1995 | Dempsey et al. | |
| 5,438,329 | 8/1995 | Gastouniotis et al. | |
| 5,579,775 | 12/1996 | Dempsey et al. | |
| 5,704,351 | 1/1998 | Mortara | |
| 5,724,025 | 3/1998 | Tavori | 340/573.1 |
| 5,745,049 | 4/1998 | Akiyama et al. | 340/870.17 |
| 5,755,230 | 5/1998 | Schmidt et al. | |
| 6,052,600 | 4/2000 | Fette et al. | 455/509 |

OTHER PUBLICATIONS

Fluke Corporation Document 3304 Rev. B, Jul. 1997.
Fluke Corporation Document 3305 Rev. B, Jul. 1997.
Fluke Data Acquisition—Wireless Logger—pp. 6 & 7.

*Primary Examiner*—Nay Maung
*Assistant Examiner*—Raymond B. Persino

[57] ABSTRACT

A programmable wireless data acquisition system, comprising a transmitting device and a receiving device. The transmitting device is capable of receiving multiple external inputs and generating and transmitting a radio frequency signal encoded with data corresponding to the inputs. The transmitting device is variably configurable to enable it to accept inputs having different characteristics and ranges and to enable it to provide variable sampling rate, gain and filtering of the inputs. The transmitting device having a microprocessor such that the microprocessor controls the operation thereof. The receiving device is capable of receiving the radio frequency signal, demodulating it and decoding the data. The receiving device has a microprocessor such that the microprocessor controls the operation thereof. External programming device programs the transmitting device and the receiving device by wired connection or through radio frequency signal.

7 Claims, 4 Drawing Sheets

PROGRAMMABLE WIRELESS DATA ACQUISITION SYSTEM

STATEMENT REGARDING FEDERALLY SPONSORED RESEARCH OR DEVELOPMENT

This invention was made with Government support under Grant No.R44NS35413 awarded by the National Institute of Neurological Disorders and Stroke and Grant No. R44MH54949 awarded by the National Institute of Mental Health. The Government has certain rights in the invention.

BACKGROUND OF THE INVENTION

1. Field of the Invention

The present invention relates, generally, to wireless data acquisition systems for data communications and, more particularly, to wireless data acquisition systems which employ small size, low power and low cost components and which may be adapted for different applications by software programming.

2. Description of the Related Art

All data acquisition systems generally operate in a similar fashion. They receive an external input from some type of sensing device, condition and/or convert the input to a format suitable for transmission, as necessary, and transmit it to another piece of equipment usually a monitor or controller, which may be a computer, and more specifically, a personal computer. The external input is generally an analog signal, although digital signals, frequently on-off switching, pulse-width modulation, or serial data protocols, are also involved. The inputs, though, come in many forms with many different characteristics, be they pneumatic, hydraulic or electronic, to list a few. Modern applications, control schemes and devices usually necessitate the use of electronic inputs in one form or another. For example, electronic analog inputs may have ranges of 4–20 mA, +/–5 volts, +/–15 volts, or microvolts to millivolts.

In the case of a wired system the analog input can be transmitted directly over interconnecting wiring with the major concern being that the interconnecting wires be suitably shielded to prevent interference by nearby electromagnetic sources. Signal conditioning becomes critically important for wireless systems, though. This is especially so when considering power consumption, size and cost factors. Because electronic inputs can have different characteristics (e.g.: high frequency or low frequency) and ranges (e.g.: microvolts to many volts), data acquisition systems are either application specific, i.e. designed to accept and condition a particular type of signal, i.e.: current, with a range of 4–20 mA for instance, or include separate discrete signal conditioning devices which consume a large amount of power and add considerable size.

Radio frequency (RF) wireless data acquisition systems can convert the input to a conditioned electronic signal which is used to modulate a carrier frequency which is then transmitted as a radio frequency signal to equipment in another location. The conditioned signal is encoded with data corresponding to the status of the input. The radio frequency signal is received, demodulated and decoded and the data is read, displayed, stored, and/or acted upon, i.e. monitored, analyzed, by equipment at the receiving point. In the United States the Federal Communications Commission (FCC) regulations govern RF transmissions, and similar agencies regulate RF transmissions in other countries, specifically as to the frequency band that can be utilized to transmit the signal and the strength of the signal. Other data transmission means, such as infrared, optical, or any means which does not require a mechanical connection is understood to offer similar advantages as RF transmission.

Wireless data acquisition systems are well known in the art. In the biomedical area, U.S. Pat. No. 5,704,351 to Mortara discloses a multiple channel biomedical digital telemetry transmitter. Mortara teaches an 8 channel biomedical transmitter specifically directed to electrocardiogram (EKG) signal transmission in the 902 to 928 MHz band. The Mortara device includes input circuitry and an analog-to-digital converter which receives the input signal from an EKG electrode and converts it to a digital signal which is inputted to a microprocessor. The microprocessor then converts the digital signal to a serial digital output signal which is used to frequency modulate the radio frequency carrier signal for telemetry transmission. The carrier frequency is adjustable within the 902 to 928 MHz band by two manual frequency setting switches. The use of these manual switches is the only adjustment available on the Mortara device and only to manually set the frequency within the 902 to 928 MHz band. The input circuitry and analog-to-digital converter are not adjustable nor adaptable to accept different input signal characteristics. In addition, the Mortara device cannot be adjusted, by programming or otherwise, to operate in any other frequency band. Finally, the Mortara device is just a transmitter and, therefore, is not able to receive RF or other signals to control its operation.

Similarly, U.S. Pat. No. 5,755,230 by Schmidt et al, discloses a device for monitoring a physiological signal, in this case EEG, and transmitting it by RF signal to a receiver. Like Mortara, the Schmidt device also cannot be modified or adjusted to receive inputs from different physiological sensors.

U.S. Pat. No. 5,579,775 to Dempsey, discloses a Dynamic Control of a Patient Monitoring System. Like Mortara and Schmidt, Dempsey '775 teaches a patient monitoring system with a telemetry subsystem which monitors and transmits an RF signal representing signals it receives from one or more physiological monitoring instruments. Unlike Mortara and Schmidt, Dempsey '775 teaches a receiving subsystem which can receive RF signals, in a backchannel arrangement to control the operation of the system. Dempsey '775, though, does not disclose or teach a system with the capabilities to adjust or modify input means, by software programming or otherwise, in response to different physiological signals. The device relies on separate monitoring sections in order to accommodate different physiological signals, i.e., EEG, ECG, $SpO_2$ etc.

U.S. Pat. No. 5,417,222, also to Dempsey, discloses a portable processor interfaceable with a telemetry monitor at its I/O port. The Dempsey '222 device includes a telemetry monitor comprising a physiological monitor which receives selected physiological signals indicating a specific physiological condition of a patient. The physiological monitor is a specific type of monitor, i.e. one that reads signals of a specific physiological function, EKG for example. In the event that a different physiological function is to be monitored, i.e. EEG, a different physiological monitor must be employed. The device taught in this patent is designed to operate with basic physiological monitors already utilized in patient diagnostic services. Actually, the Dempsey '222 patent really only teaches the interface of a programmable processor, an example of which is given as Hewlett Packard 100LX palmtop processor (Hewlett Packard being listed as assignee of the patent) with a physiological monitor. Like the device in Dempsey '775, the device is not able to adapt or change the physiological monitor, by software or otherwise, to accept different physiological signals.

Fluke Corporation markets a wireless data acquisition system entitled "Wireless Logger".

The system is an integration of Fluke's Hydra Data Logger, a portable instrument monitor/analyzer, which accepts wired external inputs, with a RF modem. The Hydra Data Logger includes a universal input module which accepts and conditions the external inputs. The resulting signals are transmitted by the modem to another modem wired to a personal computer. The separate modem and universal input module are relatively large and consume up to 10 watts of power. In addition, the operation of the system is not software programmable. RF Neulink markets a similar system utilizing the VHF (136–280 MHz) and UHF (403–512 MHz) bands.

Accordingly, a need exists for a programmable wireless data acquisition system having a signal processing module which is capable of accepting multiple external inputs having different characteristics and ranges, and is able, through software programming, to convert and condition these external inputs, generate a radio frequency signal encoded with data corresponding to the external inputs, be frequency agile and adaptable, and transmit said radio frequency signal to a base station. In addition, a need exists for such a programmable wireless data acquisition system employing small size, low power consumptive and low cost components. Finally, a need exists for such a system which can accurately and dependably transmit data.

BRIEF SUMMARY OF THE INVENTION

The present invention provides a method and apparatus to satisfy the aforementioned need.

Accordingly, an object of the present invention is to provide a programmable wireless data acquisition system which is capable of accepting multiple external inputs having different characteristics and ranges.

Another object of the present invention is to provide a programmable wireless data acquisition system which is small, has low power consumption and contains low cost components.

Still another object of the present invention is to provide a programmable wireless data acquisition system which can adapt to any changes in the character, type or range of external inputs while the system is operating without affecting or discontinuing its operation.

Still another object of the present invention is to provide a programmable wireless data acquisition system which can be reconfigured easily by minor component changes.

Accordingly, the present invention relates to a programmable wireless data acquisition system comprising a signal processing module containing a module microcontroller having a memory. The signal processing module operation includes inputting, conditioning and processing at least one external input having a certain range, character and type, and transmitting by wireless means a signal encoded with data corresponding to said external input. The module microcontroller adapts the signal processing module in response to variation in the range, character and type of the external input such that the adaptation occurs during signal processing module operation.

In another aspect, the present invention relates to a programmable wireless data acquisition system, comprising a signal processing module having certain components populated therein and having a module microcontroller having a memory. The signal processing module operation includes inputting, conditioning and processing at least one external input and transmitting by wireless means a signal encoded with data corresponding to the external input. The signal processing module being adaptable to varying characteristics and ranges of different of the external inputs by reconfiguring the component population of the signal processing module.

In yet another aspect, the present invention relates to a programmable wireless data acquisition system, comprising a signal processing module comprising a module microcontroller having a memory. The signal processing module operation includes inputting, conditioning and processing at least one external input and transmitting by wireless means a signal encoded with data corresponding to the external input. The at least one external input comprising at least one physiological signal wherein the physiological signal is from the group of physiological signals consisting of EEG, EKG, EOG, $SpO_2$, $PO_2$, $PCO_2$ EMG, blood pressure, heart rate, pulse, body temperature, air flow and respiration. The module microcontroller adapts the signal processing module in response to variation in the range, character and type of the physiological signal such that the adaptation occurs during signal processing module operation.

In still yet another aspect, the present invention relates to a programmable wireless data acquisition system, comprising a signal processing module containing a module microcontroller having a memory, a module transmitter and a module receiver. The signal processing module operation includes inputting, conditioning and processing at least one external input having a certain range, character and type, and transmitting a radio frequency signal encoded with data corresponding to the external input. The module microcontroller through the module receiver receives a radio frequency signal with instructions for adapting the signal processing module in response to variation in the range, character and type of the external input such that the adaptation occurs during signal processing module operation.

BRIEF DESCRIPTION OF THE SEVERAL VIEWS OF THE DRAWINGS

Further features of the present invention will become apparent to those skilled in the art to which the present invention relates from reading the following specification with reference to the accompanying drawings in which.

DETAILED DESCRIPTION OF THE INVENTION

Figure 1:
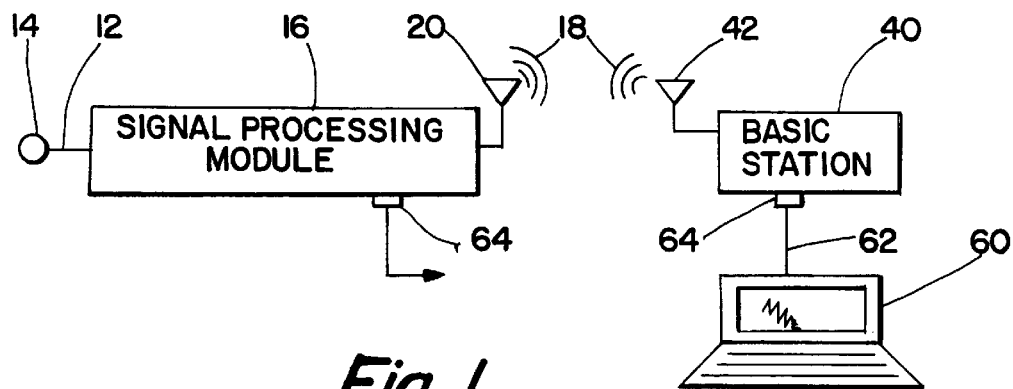
FIG. 1 is a block diagram of the present invention.

Referring now to the drawings and, in particular to FIG. 1, there is shown a block diagram of the present invention. An external input 12 from sensor 14 is inputted to signal processing module 16. Although, one sensor 14 and one external input 12 are shown, the signal processing module 16 is capable of accepting multiple external inputs 12 from multiple sensors 14. The signal processing module 16 generates a signal 18 encoded with data corresponding to the external input 12. The signal processing module 16 transmits the signal 18 by wireless means. to base station 40 In FIG. 1, the wireless means is shown as radio frequency (RF). In this case, the signal processing module generates a radio frequency signal 18 by frequency modulating a frequency carrier and transmits the radio frequency signal through module antenna 20. The base station 40 receives the radio frequency signal 18 through base antenna 42, demodulates the radio frequency signal 18, and decodes the data. It is understood that other wireless means can be utilized with the present invention, such as infrared and optical, for example. Although one module antenna 20 and one base antenna 42 is shown in this embodiment, it is understood that two or more diversity antennas can be used and are included in the present invention. An external programming means 60, shown in FIG. 1 as a personal computer, contains software which is used to program the signal processing module 16 and the base station 40 through data interface cable 62. The data interface cable 62 is connected to the base station 40 and signal processing module 16 by respective connectors 64. The same data interface cable 62 or two different interface cables 62 can be used, one for the base station 40 and one for the signal processing module 16. The signal processing module 16 and the base station 40 can be programmed by connecting a data interface cable 62 between it and an external programming means 60 or by radio frequency (or other type) of signals transmitted between a base station 40 to the signal processing module 16 or to another base station 40. RF signals, therefore, can be both transmitted and received by both signal processing module 16 and base station 40. In this event the signal processing module 16 also includes a module receiver 29 while the base station 40 also includes a base transmitter 84, in effect making both the signal processing module 16 and the base station 40 into transceivers. In addition, the data interface cable 62 also can be used to convey data from the base station 40 to the external programming means 60. If a personal computer is the external programming means 60, it can monitor, analyze and display the data in addition to its programming functions. The base receiver 80 and module receiver 29 can be any appropriate receivers, such as direct or single conversion types., The base receiver 80 preferably is a double conversion superheterodyne receiver while the module receiver 29 preferably is a single conversion receiver. Advantageously, the receiver employed will have automatic frequency control to facilitate accurate and consistent tuning of the radio frequency signal 18 received thereby.

Figure 2:
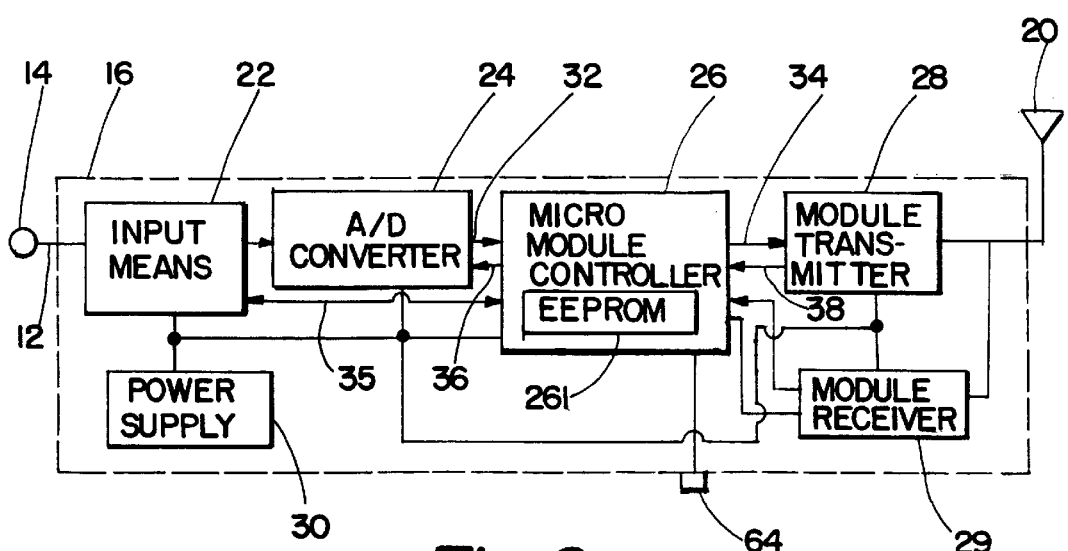
FIG. 2 is a block diagram of the signal processing module of the present invention.
Figure 3:
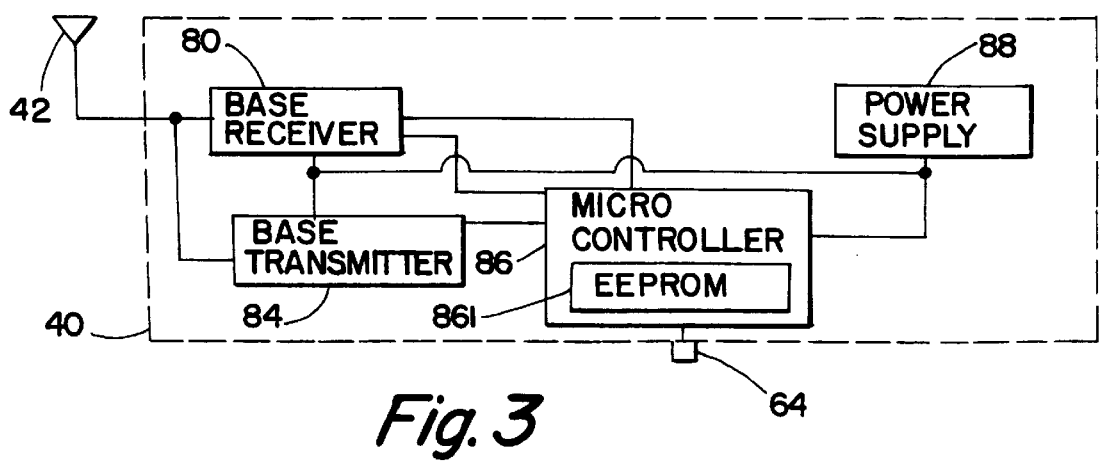
FIG. 3 is a block diagram of the base station of the present invention.

Referring now to FIG. 2, there is shown a block diagram of the signal processing module 16 with the sensor 14 and the module antenna 20. The signal processing module 16 comprises input means 22, analog-to-digital (A/D) means 24, a module microcontroller 26 with a nonvolatile memory, advantageously, an EEPROM 261, a module transmitter 28, a module receiver 29 and a module power supply 30. Although the module antenna 20 is shown externally located from the signal processing module 16, it can also be incorporated therein. The module antenna 20 may be a printed spiral antenna printed on a circuit board or on the case of the signal processing module 16 or other type of antenna. A module power supply 30 provides electrical power to the signal processing module 16 which includes the input means 22, A/D means 24, module microcontroller 26 module transmitter 28 and module receiver 29.

The input means 22 is adjustable either under control of the module microcontroller 26 or by means of individually populatable components based upon the specific external input 12 characteristics and range enabling the input means 22 to accept that specific external input 12. For example, if the input is a 4–20 mA analog signal, the input means 22 is programmed by the module microcontroller 26 and/or populated with the components needed to accept that range and characteristic of signals. If the input characteristics change the programming and/or components change accordingly but the same platform circuit board design is utilized. In other words, the same platform design is utilized notwithstanding the character, range, or quantity (number of external inputs 12) [up to a predetermined limit] of the input. For example, bioelectric signals such as EEG, EMG, EKG, and EOG have typical amplitudes of a few microvolts up to a few tens of millivolts. For a given application, a specific frequency band of interest might be from 0.1 Hz to 100 Hz, whereas another application may require measurement of signals from 20 Hz to 10 KHz. Alternatively, measurement of vital signs such as body temperature and respiration rate may deal with signals in a range of +5 volts, with a frequency content from DC (0 Hz) to 20 Hz. For other applications such as industrial process monitoring, the information of interest may be contained in the signal as a current, such as a 4 to 20 mA current loop sensor, or it may take the form of resistance, impedance, capacitance, inductance, conductivity, or some other parameter, The present invention provides a single device for measuring such widely disparate signal types and presents distinct economic advantages, especially to small enterprises such as a medical clinic located in a rural area, which would be empowered by this invention to conduct tests which would otherwise have required patient travel to a large medical center, with all the attendant cost thereof.

This is possible due to the selectively adaptable input means 22 and A/D means 24, the frequency agile module transmitter 28 and base transmitter 84, and the programmability of the module microcontroller 26 and EEPROM 261. One universal platform design then can be utilized for all applications. In addition, the signal processing module can comprise multiple copies of the input means 22 and the A/D means 24. Cost savings can be achieved by multiplexing at several different points in the input means 22 and the A/D means 24 allowing hardware to be shared among external inputs 12.

After receipt by the input means 22, the external input 12 is inputted to the A/D means 24. The A/D means 24 converts the input to a digital signal 32 and conditions it. The A/D means 24 utilizes at least one programmable A/D converter. This programmable A/D converter may be an AD7714 as manufactured by Analog Devices or similar. Depending upon the application, the input means 22 may also include at least one low noise differential preamp. This preamp may be an INA126 as manufactured by Burr-Brown or similar. The module microcontroller 26 can be programmed to control the input means 22 and the A/D means 24 to provide specific number of external inputs 12, sampling rate, filtering and gain. These parameters are initially configured by programming the module microcontroller 26 to control the input means 22 and the A/D means 24 via input communications line 35 and A/D communications line 36 based upon the input characteristics and the particular application. If the application changes, the A/D converter is reconfigured by reprogramming the module microcontroller 26. In this manner, the input means 22 and the A/D means 24 can be configured to accept analog inputs of 4–20 mA, +/−5 volts, +/−15 volts or a range from +/−microvolts to millivolts. They also can be configured to accept digital inputs, for detection of contact closure, for example.

The module microcontroller 26 controls the operation of the signal processing module 16. In the present invention, the module microcontroller 26 includes a a serial EEPROM 261 but any nonvolatile memory (or volatile memory if the signal processing module remains powered) can be used. The EEPROM 261 can also be a separate component external to the module microcontroller 26. Advantageously, the module microcontroller 26 may be PIC16C74A PIC16C74B or a PIC16C77 both manufactured by MicroChip, or an Amtel AT90S8515 or similar. The module microcontroller 26 is programmed by the external programming means 60 through the connector 64 or through radio frequency signal from the base station 40. The same module microcontroller 26, therefore, can be utilized for all applications and inputs by programming it for those applications and inputs. If the application or inputs change, the module microcontroller 26 is modified by merely reprogramming. The digital signal 32 is inputted to the module microcontroller 26. The module microcontroller 26 formats the digital signal 32 into a digital data stream 34 encoded with the data from the digital signal 32. The digital data stream 34 is composed of data bytes corresponding to the encoded data and additional data bytes to provide error correction and housekeeping functions. Advantageously, the digital data stream 34 is organized in data packets with the appropriate error correction data bytes coordinated on a per data packet basis. These packets can incorporate data from a single input channel or from several input channels in a single packet, or for some applications may advantageously include several temporally differing measurements of one or a plurality of input channels in a single packet. The digital data stream 34 is used to modulate the carrier frequency generated by the transmitter 28.

The module transmitter 28 is under module microcontroller 26 control. The module transmitter 28 employs frequency synthesis to generate the carrier frequency. In the preferred embodiment, this frequency synthesis is accomplished by a voltage controlled crystal reference oscillator and a voltage controlled oscillator in a phase lock loop circuit. The digital data stream 34 is used to frequency modulate the carrier frequency resulting in the radio frequency signal 18 which is then transmitted through the module antenna 20. The generation of the carrier frequency is controlled by the module microcontroller 26 through programming in the EEPROM 261, making the module transmitter 28 frequency agile over a broad frequency spectrum. In the United States and Canada a preferred operating band for the carrier frequency is 902 to 928 MHz. The EEPROM 261 can be programmed such that the module microcontroller 26 can instruct the module transmitter 28 to generate a carrier frequency in increments between 902 to 928 MHz. as small as about 5 to 10 KHz. In the US and other countries of the world, the carrier frequency may be in the 2400 to 2483.5 MHz. band, 5.725 to 5.875 GHz. band, or the 24.0 to 24.25 GHz. band, or other authorized band. This allows the system to be usable in non-North American applications and provides additional flexibility.

The voltage controlled crystal oscillator (not shown) in the module transmitter 28, not only provides the reference frequency for the module transmitter 28 but, advantageously also, provides the clock function 38 for the module microcontroller 26 and the A/D means 24 assuring that all components of the signal processing module 16 are synchronized. An alternate design can use a plurality of reference frequency sources where this arrangement can provide certain advantages such as size or power consumption in the implementation.

The module receiver 29 in the signal processing module 16 receives RF signals from the base station 40. The signals from the base station 40 can be used to operate and control the signal processing module 16 by programming and reprogramming the module microprocessor 26 and EEPROM 261 therein.

The base station 40 has a base antenna 42 through which RF signals 18 are received. Base microcontroller 86 controls the operation of the base station 40 including base receiver 80, base transmitter 82, and base power supply 88. Base receiver 80 receives the RF signal 18 from base antenna 42. The base receiver 80 demodulates the RF signal 18 and the base microcontroller 86 removes any error correction and performs other housekeeping tasks. The data is then downloaded through connector 64 to the external programming means 60 or other personal computer (PC) or data storage/viewing device for viewing in real time, storage, or analysis.

Figure 4:
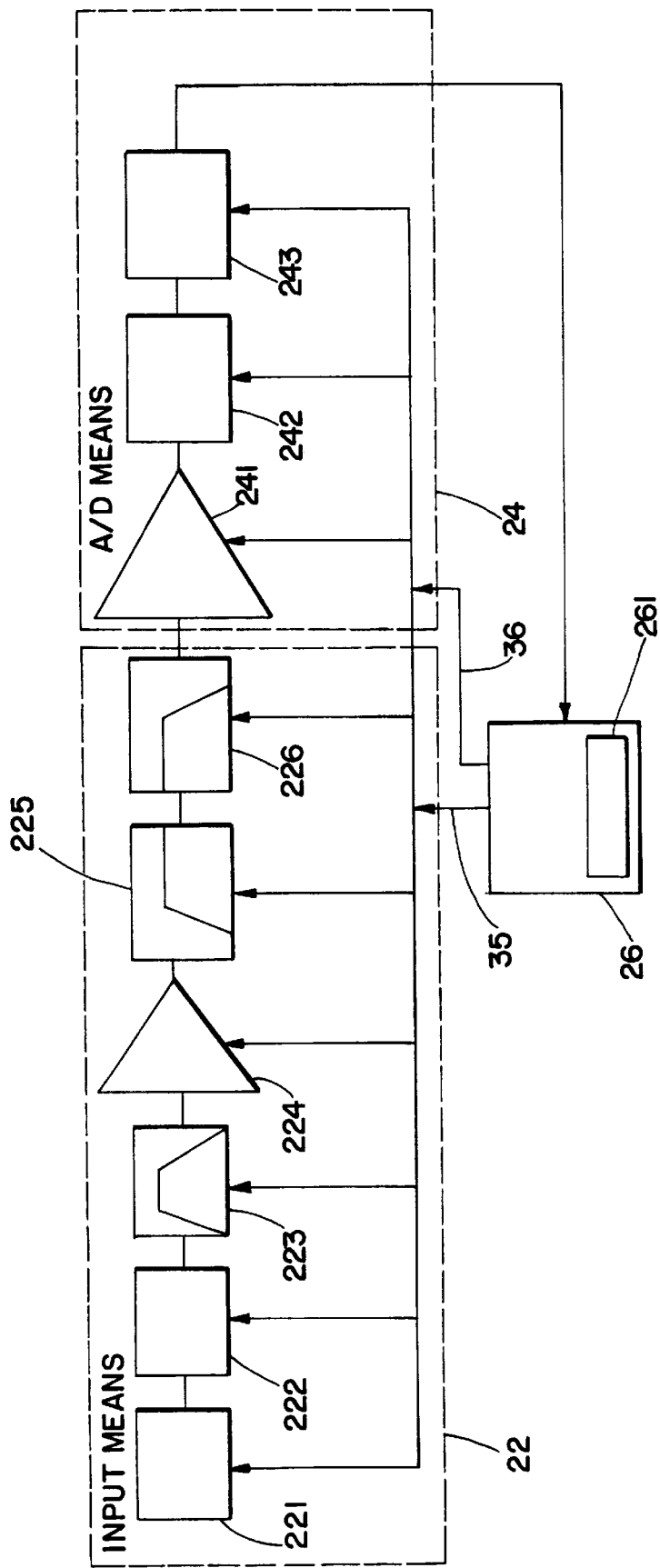
FIG. 4 is a block diagram showing the data acquisition function of the present invention in the signal processing module.

Referring now to FIG. 4, there is shown a block diagram of the input means 22 and A/D means 24 of the signal processing module 16, which provides for the data acquisition function of the present invention. The signal processing module 16 is variably configurable through software programming initiated by the external programming means 60 to the EEPROM 261 of the microcontroller 26. The variable configurability enables the signal processing module 16 to receive external inputs 12 having different characteristics and ranges and to provide variable sampling rate, filtering and gain of the external inputs 12 based upon such characteristics and range and/or the specific application. For example, if the present invention is utilized in a biomedical environment, EEG diagnosis and monitoring for instance, the sampling rate will need to be much higher than it would be for an industrial setting measuring thermocouple readings. The ability to reconfigure the system for varying signal characteristics arises at three separate levels in the present invention. For maximum flexibility, such reconfiguration can be carried out during a series of measurements by means of the wireless link, which is understood in this context to be bidirectional. Depending on the characteristics of the received signal 18, the base station 40 can command the signal processing module 16 to reconfigure the input means 22 and/or A/D means 24 to accept an external input 12 of larger amplitude, or a different frequency range, where signal characteristics change significantly during the course of a series of measurements. Alternatively, for cost, size, and power advantages, this adjustment could be carried out prior to a series of measurements, with the configuration information stored in memory in the signal processing module 16, where this memory is advantageously implemented in a nonvolatile form such as EEPROM 261, allowing the configuration information to be retained, for instance, across power outages and obviating the need for module receiver 29 and base transmitter 84, saving cost. A third alternative, which provides advantages in certain technical parameters, is to arrange the implementation of the signal processing module 16 such that minor changes in component values or parameters can reconfigure the same basic hardware to accept widely divergent external input 12 types. This reconfiguration could take place at the factory, providing cost and inventory advantages to the manufacturer, or it could be performed by the end user, providing similar cost advantages to the user in allowing one piece of equipment to perform multiple tasks.

A number of configurable components are shown in FIG. 4. Any given component of this arrangement, though, may be omitted, and, in some cases, the order of the components may be changed to gain certain advantages such as physical size, power consumption, or cost, without changing the basic spirit of the invention. Components in this FIG. 4 may be combined, either by having a single component carry out the function of two or more of the components shown or by combining functions within a single package such as an integrated circuit or hybrid module. Certain components may also operate with a fixed configuration, limiting the flexibility of certain parameters while retaining the advantages of configurability in other components.

The external input 12 inputs to the input protection network 221, which protects the signal processing module 16 against damage caused by faults or unanticipated conditions encountered at the external inputs 12. Depending on the rigors expected to be encountered in any given application and the tolerance to size and weight, the input protection network 221 may be omitted, may consist of a simple resistor network, or may include more elaborate protection such as diodes, zener diodes, transorbs, gas discharge tubes, and other components commonly known to those of ordinary skill in the art. Typically, the input protection network 221 is not configurable but its configurability in the present invention provides advantages in certain applications. Configuration options can include adjustable limits on input voltage and/or current as well as rates of change of those parameters, and other electrical parameters as well. These configuration changes can be achieved by changes to component values on a common platform for smallest size, or can be changed under processor control by means of various switches such as relays. A signal within normally expected ranges passes essentially unchanged to the measurement type means 222.

The measurement type means 222 allows selection of the external input 12 configuration. The measurement type means 222 may be used to configure the input circuitry to accept external inputs 12 which are single-ended voltage (a voltage with respect to a common reference shared between several signals), differential voltage (voltage between two defined conductors), differential current (current flowing through a conductor), single-ended current (current flowing to a common reference), frequency, capacitance, inductance, resistance, impedance, conductivity, or any other electrical parameter. The measurement type means 222 converts the external input 12 to a common parameter such as voltage or current, which can be interpreted by the succeeding blocks regardless of the original type of external signal 12 measured. One input channel can be built with several different measurement type means, which can be selectively enabled by means of an analog switch, such as that found in the AD7714 chip in the present invention. It is understood that the AD7714 chip can provide many of the functions of the A/D means 24 and the input means 22 thus reducing the overall size of the signal processing module 16. In the preferred embodiment, the output of the measurement type means 222 is a varying voltage carrrying the information which was present in the original signal, or in certain cases, a series of voltage measurements, which are then conveyed to the prefilter 223.

The prefilter 223 allows rejection of external inputs 12 of large signals which are outside the frequency band of interest, so that such signals do not saturate the low-noise preamplifier 224. The prefilter 223 can be advantageously arranged to be a relatively simple filter to provide cost, size, and power advantages, because it need only reject out of band signals to the extent necessary to protect the low-noise preamplifier 224. A typical application might use a simple "R-C" filter to reject offset voltages in an AC-coupled application, or to reject extremely high frequencies which fall well beyond the frequency band of interest, or a combination of the two. Configurability of this section can be limited to simply enabling or bypassing the prefilter 223, or may be more elaborate in allowing selection of cutoff frequencies. In the preferred embodiment this prefilter consists of a simple RC filter which can be bypassed under firmware control, to minimize noise injection; however, an alternate embodiment could incorporate electrically adjustable components such as electronic potentiometers or varactors to provide even more flexibility at the expense of size and noise injection. The prefiltered signal is then pased to the low-noise preamplifier 224.

The low-noise preamplifier 224 is advantageous in certain applications to allow application of gain to the external input 12 early in the signal chain, before significant noise is introduced by the inherent characteristics of certain components, such as thermal noise. Configurability of the gain applied at this step provides an advantage in allowing the present invention to accept larger external inputs 12 using a low gain (unity gain or lower), or alternatively to accurately measure very small external inputs 12 with minimal noise by using higher gain. This gain can be selectively chosen to be either a fixed value or unity gain under processor control by means of the signal selector built into the AD7714 used in the preferred embodiment, or can be designed to allow a selection of one of several gains by means of analog switches combined with a plurality of gain setting resistors. Gain applied at this stage has the net effect of dividing any downstream noise by the gain factor applied here. This more robust signal output by the preamplifier 224 is then passed to the AC coupling filter 225.

The AC coupling filter 225 is a highpass filter used to allow the system to reject the DC offset or steady state value of an external input 12 wherein the offset is not of interest, allowing additional gain to be applied to the changes in the external input 12. For instance, bioelectric signals such as EEG, EMG, or ECG are normally of interest only for the changes in those signals, and the absolute offset level is not of interest for diagnostic purposes. The cutoff frequency may be configured to allow adjustment of various parameters such as settling time, or may be adjusted to zero to effectively bypass the AC coupling filter 225. In the preferred embodiment, the filter may be bypassed by use of the signal selector switch in the AD7714; however, the use of adjustable components such as electronic potentiometers or varactors would allow more flexibility in choosing the cutoff frequency, at the expense of size and power consumption. The resulting signal, now stripped of any interfering DC offset if so configured, is then passed to the antialias filter 226.

The antialias filter 226 is a lowpass filter required to guard against false signals caused by aliasing between external input 12 content and sampling rate of downstream sampling functions such as multiplexing or analog-to-digital conversion. The Nyquist sampling theorem shows that any frequency content in the sampled signal which is higher than one-half the sampling rate of the sampling function will cause aliasing, which results in false signals. In practice the antialias filter 226 is more commonly set to a smaller fraction of the sampling rate, usually between ¼ and ¹⁄₁₀ the sampling rate. Regardless of the rate or ratio used, the cutoff frequency of the antialias filter 226 must change when the sampling rate changes significantly, to retain the most advantageous ratio of the sampling rate to the filter passband. The programmable cutoff frequency of the antialias filter 226 is thus required to allow for variable sampling rates. In the preferred embodiment, the high sampling rate of the delta sigma modulator in the AD7714 permits the use of a simple fixed RC type filter, with the anitalias filtering begin provided as an inherent digital filter in the AD7714; however, an alternate embodiment might use a switched capacitor filter such as the MAX7409 or other filter with a programmable cutoff frequency. The resulting filtered signal is then conveyed to the programmable gain amplifier 241 in the A/D means 24.

The programmable gain amplifier 241 adjusts the external input 12 amplitude to match the amplitude accepted by the A/D converter 242. In the preferred embodiment this programmable gain amplifier is included in the AD7714 integrated circuit, but this function could also be provided with a dedicated programmable gain amplifier, or alternatively through the use of analog switches or adjustable components such as potentiometers or DACs. If too much gain is applied, the programmable gain amplifier 241 itself or downstream components will saturate, introducing severe distortion and usually rendering the external input 12 unmeasureable. If, on the other hand, insufficient gain is applied here, the quantization noise of the analog-to-digital conversion process comes to dominate the external input 12, causing a severe degradation in the signal-to-noise ratio. For instance, a typical 16-bit A/D converter 242 can distinguish between $2^{16}$ or 65536 distinct levels. With an A/D converter 242 input range of ±3 volts, each level reperesents 92 $\mu$V. If insufficient gain is applied to the external input 12 such that the total signal swing is only 200 $\mu$V, the A/D converter 242 will convert at most three distinct levels, rendering fine features of the external input 12 totally illegible. The module microcontroller 26 therefore adjusts the gain applied in the programmable gain amplifier 241 such that the expected external input 12 as processed and filtered by the preceding elements as described above, is amplified to cover as much of the A/D converter 242 input range as practical, or some other gain which optimizes signal features of interest. Additionally, in some applications it is advantageous to have the module microcontroller 26 adjust this gain dynamically depending upon the actual measured external input 12. For instance, the module microcontroller 26 might increase the programmable gain amplifier 241 gain when a measured external input 12 is very small, and then decrease the gain to avoid saturation when the external input 12 amplitude increases. This automatic gain control provides an increase in the total dynamic range achievable by the system without requiring expensive, large, and power-hungry components such as very high resolution A/D converters 242. The signal resulting from application of the specified gain is then passed to the A/D converter 242.

At least two parameters of a typical A/D converter 242 can be readily adjusted to achieve various goals as the situation dictates. First, the sampling rate may be adjusted to balance the conflicting goals of high fidelity measurements and low digital data rate. Where a signal has no high frequency content of interest, the sampling rate may be adjusted to a very low rate to minimize the demands on downstream processes such as digital filtering or telemetering of the data. On the other hand, sampling an external signal 12 with significant high-frequency content of interest demands a higher sampling rate. In the preferred embodiment, the sampling rate is programmable via the AD7714; in other implementations the sampling rate can be made adjustable by means of an externally applied sampling clock to an A/D converter. The adjustable sampling rate allows the controller to adapt the A/D converter 242 to best meet the system demands of the moment.

In a similar fashion, selection of the resolution provided by the A/D converter 242 must balance faithful reproduction of the external input 12 against total digital data rate. Depending on the particular A/D converter 242 used, there may also be a tradeoff of the maximum achievable sampling rate against the selected resolution, wherein selection of a higher resolution lowers the maximum attainable sampling rate. Again the module microcontroller 26 can adjust this parameter to best meet the system requirements, selecting higher resolution when smaller changes in the measured signal amplitude must be reported, and lower resolution when the lack of such a requirement allows advantages in the form of either a higher sampling rate or a lower digital data rate. In the preferred embodiment, the AD7714 can be programmed to either 16 bit or 24 bit resolution, and the firmware running in the microcontroller can selectively transmit 8, 12, 16, or 24 bits of the acquired data. The digital filter 243, the module microcontroller 26, or other downstream process can also reject certain portions of the digital data stream to provide an effective decrease in resolution where this decrease is advantageous, especially when the data must later cross a bandwidth-limited link such as a RF, IR or optical link. The A/D converter 242 passes the signal, now in the form of a succession of digital values, to the digital filter 243 for further processing.

The digital filter 243 extracts external input 12 parameters of interest while rejecting other signals, commonly referred to as noise. Implementation of the digital filter 243 could alternatively be in the form of analog filters applied anywhere in the signal chain prior to the A/D converter 242, but implementation as a digital filter 243 provides advantages as to programmability, calibration, drift, and accuracy. The digital filter 243 could be implemented in many forms, depending upon the demands of the particular application. In the preferred embodiment, the digital filter is inherent in the analog to digital conversion process inside the AD7714, but it is understood that the digital filter 243 could be implemented as firmware inside the module microcontroller 26 itself, or as a digital signal processor, or as a specialized integrated circuit, or by some other means. Regardless of implementation, the programmability of the digital filter 243 allows the system to readily adapt to changing measurement requirements, whether those changes are brought about by changes in the environment, changes in the external input 12 itself, or changes in the focus of the overall system. The resulting output from the digital filter 243 is a stream of digital values, ready for further processing such as assembly into the desired format for transmission by the firmware.

Figure 5:
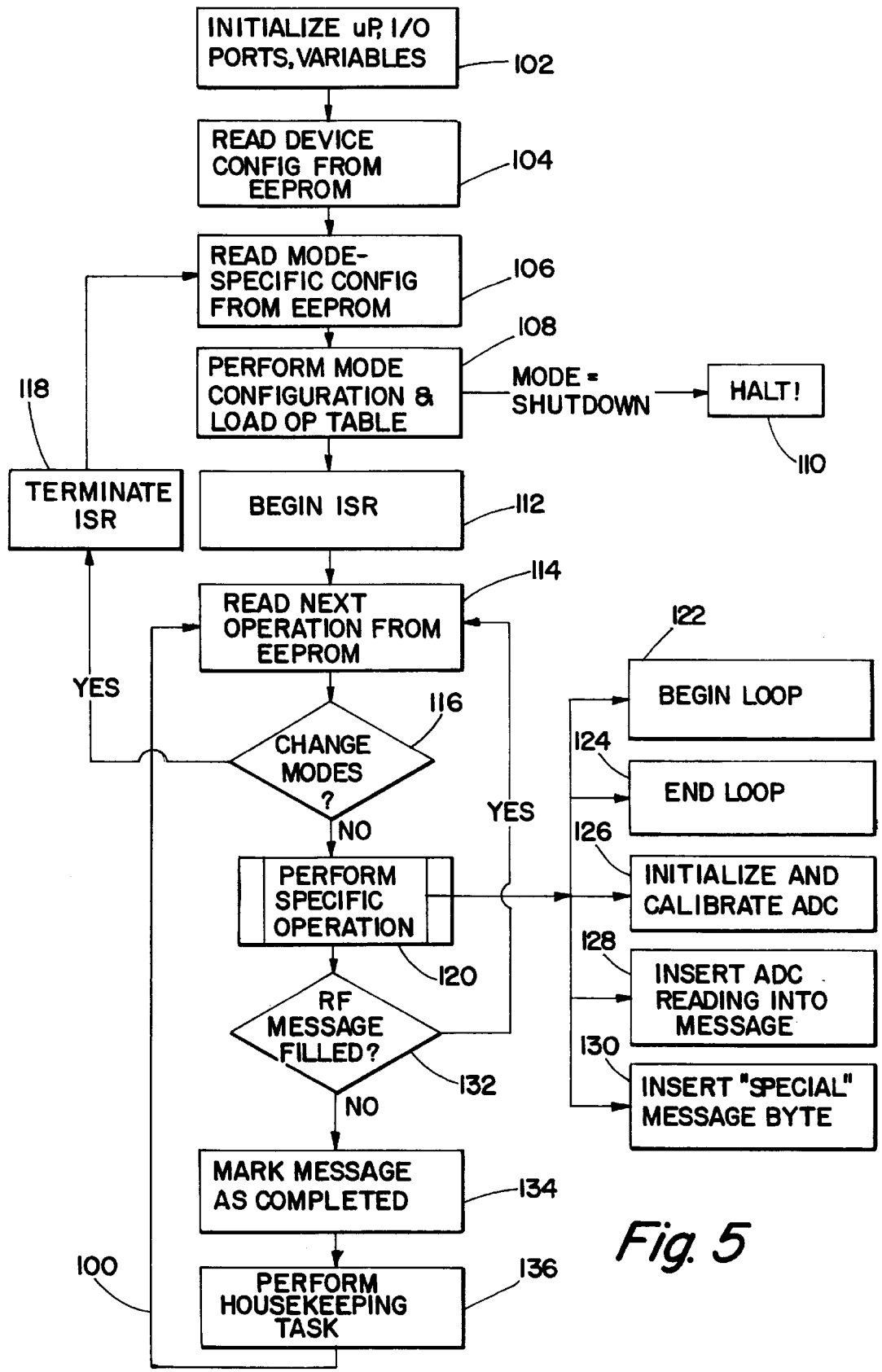
FIG. 5 is a block diagram of the programming of the firmware in the signal processing module.

Referring now to FIG. 5 there is shown a block diagram of the firmware of the present invention. The signal processing module 16 firmware defines several modes of operation 100. There are several "test" modes which are used during factory calibration of the device. In addition, there are several operation modes which have mode-specific configuration. For example, the signal processing module 16 can be programmed to operate in a first operational mode in which it transmits calibration data (used to properly zero the analog inputs) for the first three seconds of operation (or for some other predetermined time), and then switches to a second operational mode which transmits analog signal information as collected from the A/D converters 242. The configuration for each mode of operation is programmed in the non-volatile memory EEPROM 261.

Once power is first applied to the signal processing module 16, the module microcontroller 26 performs the basic device initialization, including proper configuration of the I/O ports and internal variables 102. Next, the module microcontroller 26 reads the initial device configuration 104 from the EEPROM 261. This configuration controls the input means 22 of the signal processing module 16, including the number of external inputs (also herein referred to as channels), the resolution of the A/D converter 242, and the sampling rate of each individual input channel. This configuration also controls the operation of the module transmitter 28 in the signal processing module 16, including the carrier frequency, modulation type, output power control, and the length in bytes of each transmitted RF message packet. This configuration also describes the initial mode of operation for the signal processing module 16.

Once the initial configuration has been read, the module microcontroller 26 enters the first mode of operation described in the configuration. It reads the mode-specific configuration 106, which includes the state of the module transmitter 28 and the analog inputs as used in the mode. This configuration can reside in EEPROM 261 or in module microcontroller 26 memory. The module microcontroller 26 then initializes all the peripheral devices according to this mode configuration 108. In the special case that this is the "shutdown" mode, the module microcontroller 26 will perform a software power-down 110.

Once the mode has been initialized, the module microcontroller 26 begins execution of the interrupt service routine (ISR) 112, which is responsible for transmitting the data in the form of messages along the modulated RF carrier. Operation of the interrupt service routine is asynchronous and distinct from the mainline code, and is described later.

The module microcontroller 26 begins execution of the mode-specific "opcodes" 114, which are a sequence of instructions contained either in EEPROM 261 or in the module microcontroller 26 memory. These opcodes are performed for each operational mode. The module microcontroller 26 reads the first operational code from the EEPROM 261 and interprets the opcode, performing an appropriate action:

If the opcode instructs the module microcontroller 26 to change modes 116, the module microcontroller 26 terminates the ISR 118 and returns to the mode initialization, and begins execution of a new operational mode;

If the opcode instructs the module microcontroller 26 to begin a loop construct 120, the module microcontroller 26 begins the loop by initializing a loop counter variable 122;

If the opcode instructs the module microcontroller 26 to end a loop construct, the module microcontroller 26 increments the loop counter variable and determines if the loop is complete 124. If not, the module microcontroller 26 resets the index of current opcode to the beginning of the loop, otherwise it sets the index of the next opcode to after the loop;

If the opcode instructs the module microcontroller 26 to initialize a single A/D converter 242, the module microcontroller 26 will perform the specified calibration 126;

If the opcode instructs the module microcontroller 26 to the read a single A/D converter 242, the module microcontroller 26 will take the reading and insert the data into the current message to be transmitted over the RF carrier 128;

If the opcode instructs the module microcontroller 26 to insert a special byte of data into the RF message, the module microcontroller 26 will insert this data into the message 130. This special message byte may include an identifier to uniquely identify the signal processing module 16, an error check field such as a cyclic redundancy check, or some data representing the internal state of the signal processing module 16 such as the RF frequency, measured temperature, etc.

After each opcode has been read and interpreted, the module microcontroller 26 determines if the RF message has been completely filled and is ready to be transmitted over the RF carrier 132. If it has, the module microcontroller 26 marks a flag variable for the interrupt service routine to begin transmitting the RF message 134.

Next, the module microcontroller 26 performs any housekeeping tasks, such as updating the RF tuning parameters based on changes in temperature, updating timers, etc. 136 Finally, the module microcontroller 26 returns to execute the next opcode in the sequence 114.

Figure 6:
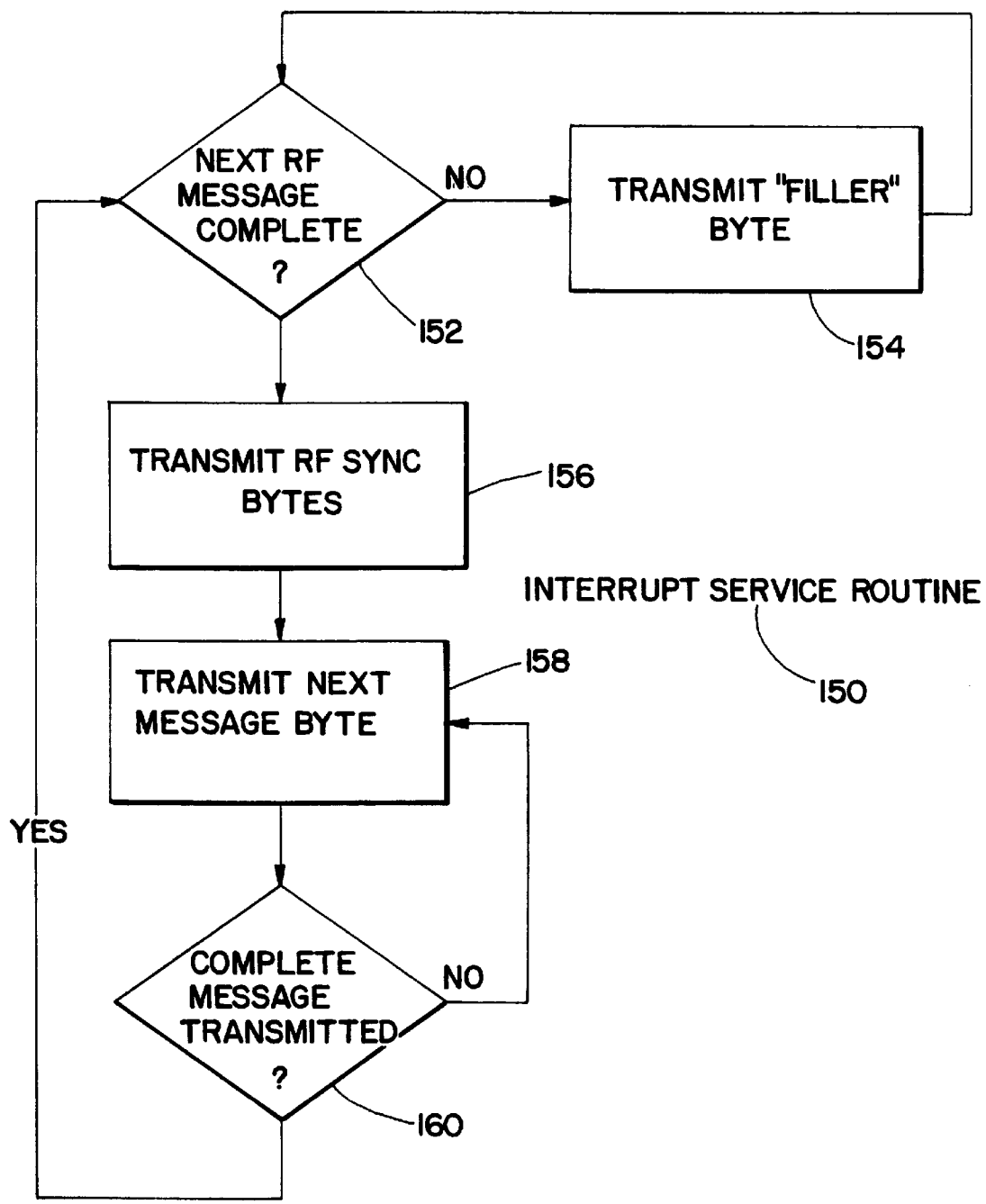
FIG. 6 is a block diagram of the programming of the interrupt service routine in the firmware of the signal processing module.

Referring now to FIG. 6 there is shown a block diagram of the software programming function of the ISR 150. The ISR is responsible for transmitting the individual message bytes over the RF carrier. The ISR is executed by a hardware interrupt which occurs immediately before every byte to be transmitted over the RF carrier. The ISR detects whether an RF mesage is completely filled 152. If the ISR detects (based on the flag variable) that an RF message is not yet completely filled by the main code, the ISR transmits a "filler" byte, or a byte with an even number of "1" and "0" bits 154. This acts to maintain an even (50%) modulation duty cycle on the carrier frequency.

Once the ISR detects that the main code has filled an RF message to be transmitted, it transmits the RF sync bytes 156. These are two unique bytes transmitted at the beginning of every RF message which are easily identified by the base station 40 as the start of a message.

Once the RF sync bytes have been transmitted, the ISR transmits each message byte of the RF message, in sequence 158. Once the RF message has been completely transmitted 160, the ISR resumes transmitting filler bytes until the next RF message is filled by the main code.

Because of the phase locked loop based frequency synthesizer used in the present invention, the module transmitter 28 and base transmitter 84 are frequency agile over the frequency range. Since the module receiver 29 and the base receiver 80 employ automatic frequency control, the present invention consumes relatively low power as the module transmitter 28 and base transmitter 84 can be intermittently powered down without loosing reception due to drift or sacrificing data transmission accuracy. The utilization of programmable firmware allows inexpensive and flexible operation for the inputting, conditioning and processing of any type, character and range of the external inputs. This also allows the module microcontroller 26, in response to the variation of the external inputs 12 or, in response to instructions received by RF signal through the module receiver 29, to adapt the signal processing module 16 based upon the variations allowing the signal processing means 16 to input, condition, process and transmit said external input notwithstanding said variation. The present invention performs this adaptation without the need to modify or alter hardware or select or use different hardware already present in the device. In other words all adaptation can be accomplished by software programming totally.

A particular embodiment of the invention has been described, but those skilled in the art will recognize that many modifications are possible that will achieve the same goals by substantially the same system, device or method, and where those systems, devices or methods still fall within the true spirit and scope of the invention disclosed. Therefore the invention should be considered to be limited in scope only in accordance with the following claims.

What is claimed is:

1. A programmable wireless physiological data acquisition system comprising a signal processing module including a microcontroller having a memory, means for remotely receiving system operating instructions, and physiological input signal receiving means, said signal processing module processing at least one external physiological input signal received by said physiological input signal receiving means, said physiological input signal having specific characteristics, said signal processing module producing an output signal encoded with data identifying said specific physiological input signal characteristics and transmitting said output signal by wireless means, said microcontroller adapting the operation of said physiological input signal receiving means in response to instructions remotely received by said system operating instruction receiving means permitting said signal processing module to process external physiological input signals having different characteristics.

2. The programmable wireless physiological data acquisition system of claim 1 wherein said signal processing module includes means for accepting and processing simultaneously multiple various external physiological input signals from multiple physiological signal sources and transmitting by wireless means an output signal encoded with data identifying said physiological input signal characteristics.

3. The programmable wireless physiological data acquisition system of claim 2 wherein said microcontroller adapts the operation of said physiological input signal receiving means in response to instructions remotely received by said system operating instruction receiving means permitting said system processing module to process simultaneously a plurality of external physiological input signals having different characteristics.

4. The programmable wireless physiological data acquisition system of claim 1 wherein said wireless means is radio frequency.

5. The programmable wireless physiological data acquisition system of claim 1 wherein said wireless means is infrared.

6. A programmable wireless physiological data acquisition system comprising a signal processing module including a microcontroller having a memory, a module transmitter, and a module receiver, said signal processing module processing at least one external physiological input signal having specific characteristics and producing an output signal encoded with data identifying said specific physiological input signal characteristics, said signal processing module transmitting said output signal via said transmitter, said microcontroller adapting the operation of said signal processing module in response to instructions remotely received via said receiver permitting said signal processing module to process external physiological input signals having different characteristics.

7. The programmable wireless physiological data acquisition system of claim 6 wherein said signal processing module includes means for processing simultaneously multiple various external physiological input signals from multiple physiological signal sources and transmitting by wireless means an output signal encoded with data identifying said physiological input signal characteristics.

* * * * *